United States Patent
Basset et al.

(10) Patent No.: US 6,469,225 B1
(45) Date of Patent: Oct. 22, 2002

(54) PROCESS FOR MANUFACTURING ALKANES

(75) Inventors: Jean-Marie Basset, Caluire; Christophe Coperet; Laurent Lefort, both of Lyons, all of (FR); Barry Martin Maunders, Woking Surrey (GB); Olivier Maury, Rennes (FR); Guillaume Saggio, Lyons (FR); Jean Thivolle-Cazat, Fontaine/Saone (FR)

(73) Assignee: BP Chemicals Limited, London (GB)

( * ) Notice: Subject to any disclaimer, the term of this patent is extended or adjusted under 35 U.S.C. 154(b) by 45 days.

(21) Appl. No.: 09/663,941

(22) Filed: Sep. 18, 2000

Related U.S. Application Data

(63) Continuation of application No. PCT/GB99/03598, filed on Oct. 29, 1999.

(30) Foreign Application Priority Data

Nov. 6, 1998 (FR) ............................................ 98/14180

(51) Int. Cl.⁷ ................................................. C07C 6/08
(52) U.S. Cl. ...................... 585/708; 585/700; 585/705; 585/931
(58) Field of Search ................................ 585/700, 705, 585/708, 931

(56) References Cited

U.S. PATENT DOCUMENTS 3,277,202 A * 10/1966 Benson, Jr. et al. .... 204/157.15
6,229,060 B1 * 5/2001 Vidal et al. ................. 585/708

FOREIGN PATENT DOCUMENTS

WO    WO 98/02244    1/1998

* cited by examiner

*Primary Examiner*—Walter D. Griffin
(74) *Attorney, Agent, or Firm*—Finnegan, Henderson, Farabow, Garrett and Dunner, L.L.P.

(57) ABSTRACT

A process for the manufacture of alkanes comprising a cross-metathesis reaction between at least one starting alkane (A) and one organometallic compound (B) fixed to an inorganic support and comprising a metal bonded to at least one hydrocarbon-comprising radical. The reaction leads to the formation of at least one other alkane (C) which is a higher or lower homologue of the starting alkane (A), by cleavage of the hydrocarbon-comprising radical with the metal of the organometallic compound (B) and recombination of the radical with at least one other radical originating from a cleavage of the starting alkane (A). The metal of the compound (B) preferably is selected from transition metals, lanthanides and actinides, and the hydrocarbon-comprising radical of the compound (B) preferably is selected from alkyl, alkylidene and alkylidyne radicals.

31 Claims, No Drawings

PROCESS FOR MANUFACTURING ALKANES

This application is a Continuation of International Application Number PCT/GB99/03598, filed Oct. 29, 1999.

PROCESS FOR MANUFACTURING ALKANES

The present invention relates to a process for the manufacture of alkanes in the presence of a supported organometallic compound which employs in particular an alkane cross-metathesis reaction.

Alkanes are generally products which are difficult to convert because of their chemical inertia. Nevertheless, the conversion of alkanes into other alkanes is known. Hydrogenolysis reactions, which consist of cleavage or opening reactions of a carbon-carbon bond by hydrogen, are known, for example. Isomerization reactions, which convert an alkane into one of its isomers, for example n-butane into isobutane, are also known. All these reactions are generally carried out at relatively high temperatures and in the presence of catalysts based on metals, in particular on transition metals, in the bulk form or in the form of films or alternatively in the form of metal particles deposited on inorganic supports essentially based on metal oxide. Thus, for example, the catalyst can be of the following type: nickel black, Ni/SiO$_2$, platinum black, Pt/SiO$_2$, Pd/Al$_2$O$_3$, or tungsten or rhodium film, optionally mixed with copper, tin or silver. With some metal catalysts, it was possible simultaneously to observe alkane homologation reactions, which consist of reactions which convert alkanes into higher alkanes. However, alkane homologation reactions are generally very minor reactions in comparison with the hydrogenolysis or isomerization reactions and their results are very poor.

Nevertheless, it remains the case that a process for the conversion of alkanes into their higher homologues would constitute a means for enhancing in value certain petroleum fractions, in particular the lightest fractions, such as the C4 or C5 fractions, or liquefied petroleum gas, also known as LPG. It is known that, as a general rule, alkanes of low molecular weight cannot be exploited to any great extent in chemistry or petrochemistry, other than as fuels, whereas heavier alkanes are often of greater commercial interest, such as, for example, to increase the octane number of engine fuels or alternatively to involve these heavier alkanes in thermal or thermal catalytic cracking or steam cracking reactions in order to manufacture, for example, olefins or dienes.

In this sense, Patent Application PCT/FR 97/01266 discloses a process for the conventional metathesis of alkanes in which at least one alkane is reacted with itself or several alkanes with one another in the presence of a solid catalyst comprising a metal hydride grafted to and dispersed over a solid oxide. Thus, a metathesis reaction is carried out in the presence of this metal hydride by cleavage and recombination of the carbon-carbon bonds, converting an alkane simultaneously into its higher and lower homologues. The reaction can be written according to the following equation (1):

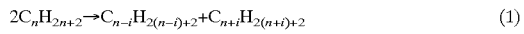

where i=1,2,3, ... n−1 and n can range from 2 to 30 and even beyond.

The catalyst based on metal hydride comprises a transition metal chosen from those from groups 5 and 6 of the Table of the Periodic Classification of the Elements (as defined by IUPAC in 1991 and illustrated in "Hawley's Condensed Chemical Dictionary", 12$^{th}$ edition, by Richard J. Lewis, Sr., published by Van Nostrand Reinhold Company, New York, 1993), such as, in particular, tantalum, chromium or tungsten. The preparation of the catalyst comprises a stage of hydrogenation of an organometallic compound comprising a transition metal dispersed over and grafted to a solid oxide beforehand, so that the transition metal is reduced to an oxidation state lower than its maximum value, thus resulting in the metal hydride. However, like any conventional alkane metathesis reaction, in particular carried out in the presence of this metal hydride, higher and lower homologous alkanes are simultaneously manufactured, which limits the degree of freedom in the choice of alkane to be manufactured, since several types of alkanes are manufactured simultaneously.

A novel process for the manufacture of alkanes has now been found which makes use in particular of an alkane cross-metathesis reaction carried out in the presence of an organometallic compound. This novel process makes it possible to give an additional degree of freedom and a greater flexibility in the synthesis of alkanes. Thus, for the first time, it has been possible to demonstrate an alkane cross-metathesis reaction which consists essentially of cleavage and recombination reactions of carbon-carbon and carbon-metal bonds between at least one startng (initial) alkane and an organometallic compound comprising at least one hydrocarbon-comprising radical. The novel process can be employed under less severe conditions than the majority of processes known to date and is capable of easily and efficiently producing more desirable alkanes of economic value with various applications according to their molecular mass.

The subject-matter of the invention is therefore a process for the manufacture of alkanes, characterized in that it comprises, as main stage, a cross-metathesis reaction between at least one starting alkane (A) and one organometallic compound (B) fixed to an inorganic support and comprising a metal bonded to at least one hydrocarbon-comprising radical, which reaction results in the formation of at least one other alkane (C), which is a higher or lower homologue of the starting alkane (A), by cleavage of the hydrocarbon-comprising radical with the metal of the organometallic compound (B) and recombination of the said radical with at least one other radical originating from a cleavage of the starting alkane (A).

Thus, the process of the invention comprises an alkane cross-metathesis reaction which consists essentially of a stoichiometric reaction between the starting alkane (A) and the organometallic compound (B). The products resulting from the reaction include in particular at least the other alkane (C) and at least one other organometallic compound (D) having a different hydrocarbon-comprising radical from that of the compound (B).

By way of illustration, the alkane cross-metathesis reaction can be written according to at least one of the following two equations (2) and (3):

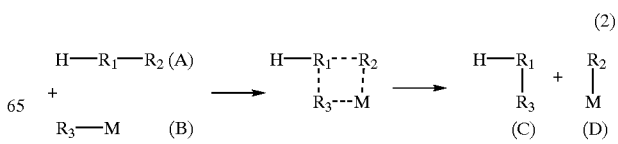

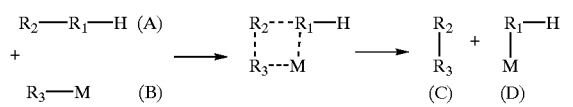

(3)

in which equations H—$R_1$—$R_2$ represents the starting alkane (A), H represents a hydrogen atom, $R_1$ and $R_2$ represent hydrocarbon-comprising radicals, and $R_3$—M represents the organometallic compound (B) with M representing the metal bonded to $R_3$, which itself represents a hydrocarbon-comprising radical.

Side reactions can take place in parallel with the alkane cross-metathesis reaction, in particular carbon-hydrogen bond cleavage and recombination reactions as described in the following equation (4):

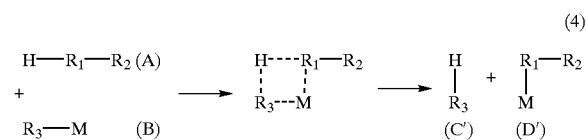

(4)

The invention thus makes it possible, by virtue of a cross-metathesis reaction, to convert the starting alkane (A) into at least one of its higher or lower homologues (C) by reactions of cleavage and of recombination with the hydrocarbon-comprising radical of the organometallic compound (B). More specifically, it makes use of cleavage reactions of carbon-carbon bonds of the starting alkane (A) and of cleavage reactions of the carbon-metal bond of the organometallic compound (B). The cleavage reactions are themselves followed by recombination reactions which form new carbon-carbon and carbon-metal bonds and thus result in at least one other alkane (C) and one other organometallic compound (D). This reaction is all the more surprising since only one conventional alkane metathesis reaction was known until now, converting, by catalytic reaction, an alkane simultaneously into one or more of its higher homologues and into one or more of its lower homologues according to, for example, the abovementioned equation (1). The alkane cross-metathesis reaction, in contrast to the conventional metathesis reaction, does not employ a catalyst, such as a supported metal hydride, but an organometallic compound which takes part as reactant in a stoichiometric reaction with an alkane.

One of the advantages of the cross-metathesis is that of being able to direct as desired the reaction towards the formation essentially of one or more desired alkanes. This can be obtained by virtue of the choice of the organometallic compound (B) and of its hydrocarbon-comprising radical which, by cleavage with the metal and recombination with another radical originating from the starting alkane, results directly in the desired alkane. In contrast, in conventional metathesis, at least two alkanes are formed simultaneously, one a higher homologue and the other a lower homologue, according to multiple cleavage and recombination reactions essentially produced at random on the starting alkane.

The cross-metathesis reaction as employed in the process of the present invention can be continued and accompanied by a conventional metathesis reaction, as represented schematically by the abovementioned equation (1). This is because it has been observed that higher and lower homologous alkanes can be formed simultaneously from the starting alkane. Furthermore, the decomposition product of the organometallic compound (B) resulting from the cross-metathesis is also capable of catalysing a conventional alkane metathesis reaction, such as that disclosed in Patent Application PCT/FR97/01266.

The starting alkane (A) employed in the process of the present invention can be a substituted cyclic or branched or linear alkane, for example a $C_2$ to $C_{80}$ alkane. It can be a matter in particular of $C_2$ to $C_{17}$ alkanes chosen, for example, from ethane, propane, isobutane, n-butane, isopentane, n-hexane, 2-methylpentane, 3-methylpentane and 2,3-dimethylbutane. The starting alkane can also be chosen from $C_{18}$ to $C_{80}$ alkanes, such as alkanes constituting waxes, in particular petroleum waxes, for example paraffin waxes (or macrocrystalline waxes) or microcrystalline waxes, and synthetic waxes, for example "Fischer-Tropsch" waxes or polyolefin waxes.

The starting alkane can be a linear or branched alkane corresponding to the general formula $C_nH_{2n+2}$ in which n is a number ranging from 2 to 80, preferably from 2 to 60, for example from 2 to 17, or from 18 to 80, for example from 18 to 60.

The starting alkane can also be a substituted cyclic alkane (with one or more rings) corresponding, for example, to the general formula $C_mH_{2m}$ in which m is a number ranging from 4 to 60, preferably from 4 to 30. It is a matter in particular of a cycloalkane substituted by at least one linear or branched alkane chain corresponding, for example, to the general formula

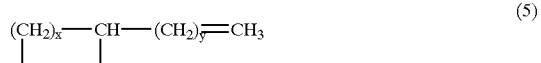

(5)

in which x is a number equal to or greater than 2, preferably ranging from 2 to 20, and y is a number equal to or greater than 0, preferably ranging from 0 to 29. In the case where the starting alkane is a substituted cycloalkane, the reaction takes place on the substituted alkane chain of the cycloalkane.

The starting alkane can be used alone or in a mixture with one or more other starting alkanes, such as those described above.

The organometallic compound (B) comprises a metal bonded to at least one hydrocarbon-comprising radical. The metal can be chosen from transition metals, in particular the metals from columns 3, 4, 5 and 6 of the Table of the Periodic Classification of the Elements mentioned above, and from lanthanides and actinides. The metal can, for example, be chosen from scandium, yttrium, lanthanum, titanium, zirconium, hafnium, vanadium, niobium, tantalum, chromium, molybdenum, tungsten, cerium and neodymium. Preference is given to a metal chosen from the transition metals of the abovementioned columns 4, 5 and 6 and in particular from titanium, zirconium, hafnium, vanadium, niobium, tantalum, chromium, molybdenum and tungsten. More particularly, preference is given to tantalum, chromium, vanadium, niobium, molybdenum or tungsten.

The metal of the organometallic compound (B) can be present at any oxidation state. It can be at an oxidation state greater than its minimum or, preferably, be at its maximum oxidation state, in particular when the metal is chosen from transition metals of the abovementioned columns 4, 5 and 6. In this group, for example, chromium and niobium are preferred at an oxidation state ranging from 4 to 6 and vanadium at an oxidation state equal to 4 or 5.

The organometallic compound (B) comprises a metal bonded to at least one hydrocarbon-comprising radical, in particular an aliphatic or alicyclic and saturated or unsaturated hydrocarbon-comprising radical and preferably a $C_1$ to $C_{20}$, in particular $C_1$ to $C_{10}$, hydrocarbon-comprising radical.

The metal can be bonded to a carbon of the hydrocarbon-comprising radical via a single, double or triple bond. The bond concerned may in particular be a single carbon-metal bond of a type: in this case, the hydrocarbon-comprising radical is an alkyl radical, for example a linear or branched radical. The term "alkyl radical" is understood to mean an aliphatic monovalent radical originating from the removal of a hydrogen atom in the molecule of an alkane or of an alkene or of an alkyne, for example a methyl ($CH_3$—), ethyl ($C_2H_5$—), propyl ($C_2H_5$—$CH_2$—), neopentyl (($CH_3$)$_3$C—$CH_2$—), allyl($CH_2$=$CH$—$CH_2$—) or ethynyl ($CH$≡$C$—) radical. The alkyl radical can be, for example, of formula R—$CH_2$—, where R itself represents a linear or branched alkyl radical.

It can also relate to a carbon-metal double bond of $\pi$ type: in this case, the hydrocarbon-comprising radical is an alkylidene radical, for example a linear or branched radical. The term "alkylidene radical" is understood to mean an aliphatic bivalent radical originating from the removal of two hydrogen atoms on the same carbon of the molecule of an alkane or of an alkene or of an alkyne, for example a methylidene ($CH_2$=), ethylidene ($CH_3$—$CH$=), propylidene ($C_2H_5$—$CH$=), neopentylidene (($CH_3$)$_3$C—$CH$=) or allylidene ($CH_2$=$CH$—$CH$=) radical. The alkylidene radical can, for example, be of formula R—$CH$=, where R represents a linear or branched alkyl radical.

The carbon-metal bond can also be a triple bond: in this case, the hydrocarbon-comprising radical is an alkylidyne radical, for example a linear or branched alkylidyne radical. The term "alkylidyne radical" is understood to mean an aliphatic trivalent radical originating from the removal of three hydrogen atoms on the same carbon of the molecule of an alkane or of an alkene or of an alkyne, for example an ethylidyne ($CH_3$—$C$≡), propylidyne ($C_2H_5$—$C$≡), neopentylidyne (($CH_3$)$_3$C—$C$≡) or allylidyne ($CH_2$=$CH$—$C$≡) radical. The alkylidyne radical can be, for example, of formula R—$C$≡, where R represents a linear or branched alkyl radical. It is preferable to have, among the alkyl, alkylidene or alkylidyne radicals, in particular the methyl, ethyl, propyl, isobutyl, neopentyl, allyl, neopentylidene, allylidene and neopentylidyne radicals.

The metal of the organometallic compound (B) can be bonded to more than one hydrocarbon-comprising radical. It can in particular be bonded to two or more identical or different hydrocarbon-comprising radicals chosen from alkyl, alkylidene and alkylidyne radicals. In particular, it can be bonded to at least one alkyl radical and to at least one alkylidene or alkylidyne radical. The number of hydrocarbon-comprising radicals bonded to a metal depends on the oxidation state of the metal: it is generally less than the latter and in particular equal to or less than the number of the oxidation state of the metal minus one.

The metal of the organometallic compound (B) which is bonded to at least one hydrocarbon-comprising radical can in addition be bonded to at least one alkoxy radical and/or one halogen atom. The alkoxy radical can correspond to the general formula R—O— in which R represents a linear or branched alkyl radical, for example a $C_1$ to $C_{10}$ radical. The alkoxy radical can be, in particular, the methoxy, ethoxy, propoxy or butoxy radical. The halogen atom can be fluorine, chlorine, bromine or iodine.

The organometallic compound (B) is fixed to an inorganic support which can be chosen from oxides or sulphides.

Preference is given to an inorganic support, such as a metal oxide or refractory oxide, or a mixture of metal oxides, for example silica, alumina, a mixture of silica and of alumina, zeolites, natural clays, aluminium silicates, titanium oxide, magnesium oxide, niobium oxide or zirconium oxide. The inorganic support can be a metal oxide or refractory oxide modified with an acid, such as a sulphated zirconia or a sulphated alumina. The inorganic support can also be a metal sulphide, such as a molybdenum or tungsten sulphide, a sulphurized alumina or a sulphurized metal oxide. It is preferable to use an inorganic support chosen from porous or non-porous silicas and aluminas, for example mesoporous silicas and aluminas having pores of 20 to 200 Å.

The inorganic support based on metal oxide or refractory oxide has the advantage of exhibiting, at its surface, oxygen atoms which can form part of the coordination sphere of the metal of the organometallic compound (B). Thus, the metal can advantageously be bonded to one or more functional groups of the inorganic support. In this case, if the inorganic support is a metal oxide or refractory oxide, the metal of the organometallic compound can be bonded to one or more oxygen atoms of the inorganic support. The presence of at least one oxygen-metal bond confers greater stability on the organometallic compound (B) while providing a strong support-metal bond.

Thus, in an illustrative fashion, the organometallic compound (B) fixed to an inorganic support can correspond to the following general configuration:

(6)

in which S represents an atom of the inorganic support, M represents the atom of the metal of the compound (B), R represents the hydrocarbon-comprising radical or radicals of the compound (B), which are identical to or different from one another, Y represents an alkoxy radical and/or a halogen atom, x is a number ranging from 1 to 3, preferably equal to 1 or 2, y is a number ranging from 0 to (n−x−1), preferably equal to 0, 1 or 2, n is a number representing the oxidation state of the metal M and z is a number at least equal to 1 and less than or equal to (n—x—y). In this definition, the metal, the hydrocarbon-comprising radical, the alkoxy radical and the halogen atom are those described above for the compound (B).

When the inorganic support comprises a metal oxide or refractory oxide, the general configuration (6) can then be written as (7):
in which configuration M, R, Y, x, y, z and n have the same definitions as above, and Me represents a metal atom or an atom of the main groups of the metal oxide or refractory oxide and 0 the oxygen atom of this same oxide. Thus, when the inorganic support is a silica or a zirconia, the general configuration (7) can then be written:
in which configurations M, R, Y, O, n, x, y, z and n have the. same definitions as above, and Me represents a silicon or zirconium atom of the inorganic support, with z in particular at least equal to 1 and less than or equal to (n−2−y) in the configuration (9).

In the same way, when the inorganic support is an alumina, the general configuration (7) can then be written as (10) or (11):
in which configurations M, R, Y, O, n, x, y, z and n have the same definitions as above, and Al represents an aluminium atom of the alumina, with z in particular at least equal to 1 and less than or equal to (n−2−y) in the configuration (11).

The organometallic compound (B) fixed to an inorganic support can be prepared in various ways. One of the preparation processes can comprise the dispersion and the grafting:

(1) of an organometallic precursor (B) having a metal and at least one hydrocarbon-comprising radical bonded to the said metal which are identical to those of the compound (B) and having in particular the general formula $$MR_{n-y}Y_y \quad (12)$$

in which M represents the atom of the metal of the compound (B), R represents the hydrocarbon-comprising radical or radicals of the compound (B), which are identical to or different from one another, Y represents an alkoxy radical and/or a halogen atom as defined above for the compound (B), n is a number representing the oxidation state of the metal M and y a number ranging from 0 to (n−1), preferably equal to 0, 1 or 2, with (n−y) equal to or greater than 1, over and to (2) an inorganic support, in particular a metal or refractory oxide, as described above.

The organometallic precursor (E) can itself be prepared by various methods known per se. Thus, for example, it can be prepared by an alkylation reaction of a halide or an alkoxide or an amide of the metal M using an organomagnesium compound or a Grignard.

The attachment or grafting of the organometallic precursor (E) to the inorganic support is preferably carried out by reacting the said precursor with the support and in particular with the functional groups of the support, such as OH groups or oxygen atoms when the support is a metal oxide or refractory oxide. The preparation is preferably carried out under an inert atmosphere, such as nitrogen or argon, and in particular under a non-reducing atmosphere, for example in the absence of hydrogen.

According to a preferred embodiment, the organometallic precursor (E) is grafted to a particularly anhydrous and water-free support. The solid support can be heat-treated beforehand in order to carry out a dehydration and/or a dehydroxylation, in particular at a temperature of 200 to 1100° C., for several hours, for example from 2 to 48 hours, preferably from 10 to 20 hours. The maximum temperature of the heat treatment is preferably below the sintering temperature of the support. Thus, for silica, a dehydration and/or a dehydroxylation can be carried out at a temperature of 200 to 500° C., for example at approximately 500° C., or else at a temperature ranging from 500° C. to the sintering temperature of the silica, in order in particular to form siloxane bridges at the surface of the support.

The grafting of the organometallic precursor (E) to the support can be carried out in various ways, in particular by an operation of sublimation of the precursor (E) or by bringing the said precursor into contact with the support in solvent or liquid medium.

In the case of a sublimation operation, the organometallic precursor, used in the solid state, is heated under vacuum and under temperature and pressure conditions which provide for its sublimation and its migration in the vapor state onto the support. The latter is preferably used in pulverulent form or in the form of pellets. The sublimation is carried out in particular between 50 and 150° C., preferably between 60 and 100° C., under vacuum. In particular, the grafting of the organometallic precursor (E) to the support can be monitored using infrared spectroscopic analysis.

In the method which has just been described, the sublimation can be replaced by an operation in which the organometallic precursor (E) and the support are brought into contact and reacted in solvent or liquid medium. In this case, the organometallic precursor (E) is preferably dissolved in an organic solvent, such as pentane or ether. The reaction is then carried out by suspending the support, preferably in a pulverulent form, in the solution comprising the organometallic precursor (E) or alternatively by any other method which provides contact between the support and the organometallic precursor (E). The reaction can be carried out at room temperature (20° C.) or more generally at a temperature ranging from −80° C. to +150° C. under an inert and preferably non-reducing atmosphere, for example a nitrogen atmosphere.

The excess organometallic precursor (E), which is not attached to the support, can be removed, for example by washing or reverse sublimation.

The process of the invention therefore comprises an alkane cross-metathesis reaction by which the starting alkane (A) is reacted with the organometallic compound (B). The reaction thus makes it possible to convert the starting alkane (A) into at least one of its higher or lower homologues by cleavage and recombination with the hydrocarbon-comprising radical of the organometallic compound (B). The choice of the starting alkane (A) and of the hydrocarbon-comprising radical of the organometallic compound (B) is important, because it directly determines the type of the alkane (C) desired and formed by the cross-metathesis reaction. All the possible combinations can be achieved from all the choices provided above for the alkane (A) and the hydrocarbon-comprising radical of the organometallic compound (B). The number of carbon atoms in the starting alkane (A) can be identical to that in the hydrocarbon-comprising radical of the organometallic compound (3): in this case, the isomeric form of the alkane (A) and the hydrocarbon-comprising radical can be identical or, preferably, different. Generally, it is preferable to choose a starting alkane (A) for which the number of carbon atoms is different from that in the hydrocarbon-comprising radical of the organometallic compound (B).

The cross-metathesis reaction between the starting alkane (A) and the organometallic compound (B) can preferably be carried out by passing the starting alkane in the gas phase over the solid compound (B). The reaction can be carried out at atmospheric pressure or above but at a pressure less than or equal to the condensation pressure of the starting alkane or of the heaviest starting alkane, when there are several starting alkanes. The reaction can also be carried out in the liquid phase in the starting alkane or in a mixture of starting alkanes with the compound (B) in suspension. The reaction can also be carried out in the presence of an inert gas, such as nitrogen, helium or argon.

The cross-metathesis reaction according to the invention can be carried out in a static reactor, that is to say with a fixed amount of reactants introduced for a complete reaction cycle, or in a recycling reactor, in which the alkanes obtained can in particular be recycled, or in a dynamic reactor, that is to say by passing a flow of the liquid or gaseous starting alkane or alkanes over a bed of the compound (B).

The cross-metathesis reaction can be carried out at temperatures varying from 20 to 400° C., preferably from 100 to 300° C., under an absolute pressure which can range from $10^{-3}$ to 10 MPa.

The process of the invention can comprise a recycling of the alkanes obtained during the reaction. It can relate equally well to the recycling of a specific alkane and to the recycling of several alkanes, in order to continue the reaction towards the production of desired alkanes. It is optionally possible to provide for separation between several alkanes, for example with the intention of recycling one alkane or another.

The cross-metathesis reaction can be carried out at temperatures varying from 20 to 400° C., preferably from 100 to 300° C., under an absolute pressure which can range from $10^{-3}$ to 10 MPa.

The process of the invention can comprise a recycling of the alkanes obtained during the reaction. It can relate equally well to the recycling of a specific alkane and to the recycling of several alkanes, in order to continue the reaction towards the production of desired alkanes. It is optionally possible to provide for separation between several alkanes, for example with the intention of recycling one alkane or another.

According to another aspect of the present invention, the process for the manufacture of alkanes can comprise one or more stages additional to the main stage. The additional stage can be carried out before or after the main stage. The additional stage can consist essentially:

either of a cross-metathesis reaction other than that of the main stage, employing, for example, at least one starting alkane (A) other than that used in the main stage, or else a different organometallic compound (B), in particular comprising at least one hydrocarbon-comprising radical other than that of the compound (B) used in the main stage, or else alternatively, simultaneously, at least one starting alkane (A) and a compound (B) which are other than those in the main stage, or of a conventional alkane metathesis reaction employing at least one starting alkane identical to or different from that used in the main stage but brought into contact with a solid catalyst comprising a metal hydride of a metal, identical to or different from the metal of the organometallic compound (B) of the main stage, chosen in particular from the metals of groups 5 and 6 of the abovementioned Table of the Periodic Classification of the Elements, in particular with an oxidation state less than its maximum value, the metal hydride being in particular grafted to and dispersed over a solid support based on metal oxide or refractory oxide, in particular as disclosed in Patent Application PCT/FR 97/01266.

When the additional stage is carried out before the main stage, the flow of the products in particular of the alkane or alkanes resulting from the additional stage, can be partially or completely used as starting material(s) (that is to say, as starting alkane(s) (A)) in the main stage according to the present invention.

When, in contrast, the additional stage is carried out after the main stage, the flow of the products resulting from the main stage according to the present invention, in particular the flow of the other alkane or alkane(s) (C), can be partially or completely used as starting material(s) (that is to say, as starting alkane(s)) in the additional stage.

The flow of the products resulting from one stage can in particular be directed continuously to the other stage, in particular when the main stage and the additional stage are themselves carried out continuously.

The process according to the present invention can be carried out continuously, in particular by a continuous addition of the starting alkane (A) to the organometallic compound (B), in particular when the latter is used in the solid state in a pulverulent form, for example in the form of a fixed or fluidized bed. The process can also be carried out continuously by continuous and simultaneous addition of the starting alkane (A) and of the organometallic compound (B), in particular when the latter is used in the form of a suspension in a liquid.

The following examples illustrate the present invention.

EXAMPLE 1

Preparation of an Organometallic Compound (B) Based on Neopentyl(neopentylidene)tantalum 800 mg of tris(neopentyl)neopentylidenetantalum (as organometallic precursor (E)), of formula

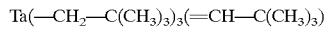

in solution in 20 ml of freshly distilled and anhydrous n-pentane, and 5 g of a silica with a specific surface of 200 m²/g, sold under the commercial reference "Aerosil"® by Degussa and dehydrated and dehydroxylated beforehand at a temperature of 500° C. for 12 hours, were introduced under an argon atmosphere into a glass reactor with a capacity of 200 ml. The mixture thus obtained at room temperature (20° C.) was kept stirred for 2 hours. At the end of this time, an ochre-coloured solid was obtained in suspension in the n-pentane. The solid was washed twice with a volume of 20 ml of n-pentane on each occasion. The solid was then dried under vacuum, which solid constituted the organometallic compound (B) fixed to silica corresponding to the general formula:

and having a tantalum content by weight of 5.2%.

EXAMPLE 2

Cross-metathesis Reaction of Isobutane 40 mg of the organometallic compound (B) prepared in Example 1 were introduced at room temperature (20° C.) into a glass static reactor with a capacity of 400 ml placed in a glove box. The atmosphere of the reactor was extracted under vacuum and isobutane was introduced therein in an amount corresponding to an absolute pressure of 0.08 MPa at room temperature. The reactor was heated, so as to raise the temperature of the latter from 20° C. to 150° C. over 10 minutes, and the reaction mixture was subsequently maintained in the reactor at 150° C. for 100 hours. At the end of this time, analysis of the gas phase in the reactor (by gas chromatography and by mass spectrometry) showed the presence:

of 2,2-dimethylbutane and 2,2,4-trimethylpentane, resulting from the cross-metathesis reaction between isobutane and the organometallic compound (B);

of neopentane, resulting from a side reaction by carbon-hydrogen bond cleavage and recombination;

and of methane, ethane, propane, 2-methylbutane, 2,4-dimethylbutane, 2-methylpentane and linear and branched C7 alkanes, resulting from the conventional metathesis reaction of isobutane.

It was observed that the cross-metathesis reaction was stoichiometric, with a yield of 80%, and that the conventional metathesis reaction of isobutane was catalytic and unfolded with a rotation (expressed as number of moles of isobutane converted per mole of tantalum) equal to 20.

EXAMPLE 3

Preparation of an Organometallic Compound (B) Based on Neopentyl(neopentylidene)tantalum 20 mg of tris(neopentyl)neopentylidenetantalum (as organometallic precursor (E)), of formula $Ta(-CH_2-C(CH_3)_3)_3(=CH-C(CH_3)_3)$ and 40 mg of a silica, sold under the commercial reference "Aerosil"® by Degussa and dehydrated and dehydroxylated beforehand at a temperature of 500° C. for 12 hours, were introduced under an argon atmosphere into a glass reactor with a capacity of 400 ml. The atmosphere of the reactor was extracted under vacuum using a vacuum pump to an absolute pressure of 10 Pa and the reactor was heated to 80° C. while maintaining a vacuum with an absolute pressure of 10 Pa. Under these conditions, the organometallic precursor (E) was sublimed and became fixed to the silica. A temperature of 80° C. and an absolute pressure of 10 Pa were thus maintained for 2 hours. At the end of this time, the excess organometallic precursor (E), which had not become fixed to the silica, was desorbed by reverse sublimation at 80° C. under an absolute pressure of 10 Pa for 1 hour. An organometallic compound (B) fixed to silica was thus obtained which corresponded to the general formula:

$(Si-O)_{1.35}Ta(=CH-C(CH_3)_3)(-CH_2-C(CH_3)_3)_{1.65}$ and which had a tantalum content by weight of 6.0%.

EXAMPLE 4

Cross-metathesis Reaction of Propane

The reaction was carried out exactly as in Example 2, except for the fact that propane was used instead of isobutane and that the organometallic compound (B) prepared in Example 3 was employed in place of that prepared in Example 1. On completion of the reaction, analysis of the gas phase in the reactor showed the presence:
- of 2,2-dimethylbutane and 2,2-dimethylpentane, resulting from the cross-metathesis reaction between propane and the organometallic compound (B);
- of neopentane, resulting from a side reaction by carbon-hydrogen bond cleavage and recombination;
- and of methane, ethane, n-butane, isobutane, 2-methylbutane, n-pentane, 2,4-dimethylbutane, 2-methylpentane, 3-methylpentane, n-hexane and linear and branched $C_7$ alkanes, resulting from the conventional metathesis reaction of propane.

It was observed that the cross-metathesis reaction was stoichiometric, with a yield of 80%, and that the conventional metathesis reaction of propane was catalytic and unfolded with a rotation (expressed as number of moles of propane converted per mole of tantalum) equal to 30.

EXAMPLE 5

Continuous Cross-metathesis Reaction of Propane 300 mg of the organometallic compound (B) prepared in Example 1 were introduced at room temperature (20° C.) into a steel dynamic reactor having a capacity of 4 ml placed in a glove box, and formed a fixed bed inside the reactor. The ambiant atmosphere of the reactor was replaced with propane which was then continuously introduced therein at a flow rate of 2 Nml/min under a total absolute pressure of 0.1 MPa, so that propane continuously flow through the fixed bed of the organometallic compound (B). The reactor was heated up to 150° C. and maintained at this temperature constantly.

Analysis of the gas at the outlet of the reactor (by gas chromatography) showed the presence of:
- 2,2-dimethylbutane and 2,2-dimethylpentane, resulting from the cross-metathesis reaction between propane and the organometallic compound
- neopentane, resulting from a side reaction by carbon-hydrogen bond cleavage and recombination, and
- methane, ethane, n-butane, isobutane and linear and branched C5–7 alkanes, resulting from the conventional metathesis reaction of propane.

What is claimed is:

1. A process for the manufacture of alkanes comprising reacting, as a main stage and by a cross-metathesis reaction, at least one starting alkane (A) with an organometallic compound (B) fixed to an inorganic support and having a metal bonded to at least one hydrocarbon-comprising radical, which reaction results in the formation of at least one other alkane (C), which is a higher or lower homologue of the starting alkane (A), by cleavage of the hydrocarbon-comprising radical with the metal of the organometallic compound (B) and recombination of said hydrocarbon-comprising radical with at least one other radical originating from a cleavage of the starting alkane (A).

2. The process of claim 1, wherein the starting alkane (A) is a substituted cyclic, branched or linear alkane.

3. The process of claim 1 or 2, wherein the starting alkane (A) is a $C_2$ to $C_{80}$ alkane.

4. The process of claim 3, wherein the starting alkane (A) is a $C_2$ to $C_{17}$ alkane.

5. The process of claim 3, wherein the starting alkane (A) is a $C_{18}$ to $C_{80}$ alkane.

6. The process of claim 1, wherein the metal of the organometallic compound (B) is selected from the group consisting of transition metals, lanthanides and actinides.

7. The process of claim 6, wherein the metal is selected from the group consisting of metals from columns 3, 4, 5 and 6 of the Table of the Periodic Classification of the Elements.

8. The process of claim 7, wherein the metal is selected from the group consisting of titanium, zirconium, hafnium, vanadium, niobium, tantalum, chromium, molybdenum and tungsten.

9. The process of claim 1, wherein the metal of the organometallic compound (B) is at an oxidation state higher than its minimum oxidation state.

10. The process of claim 1, wherein the metal of the organometallic compound (B) is a transition metal at its maximum oxidation state.

11. The process of claim 1, wherein the organometallic compound (B) has at least one saturated or unsaturated, aliphatic or alicyclic, $C_1$ to $C_{20}$ hydrocarbon-comprising radical.

12. The process of claim 1, wherein the hydrocarbon-comprising radical of the organometallic compound (B) is selected from the group consisting of alkyl, alkylidene and alkylidyne radicals.

13. The process of claim 1, wherein the metal of the organometallic compound (B) is bonded to at least one alkyl radical and to at least one alkylidene or alkylidyne radical.

14. The process of claim 1, wherein the inorganic support of the organometallic compound (B) is selected from the group consisting of metal oxides, metal sulphides, refractory oxides and refractory sulphides.

15. The process of claim 1, wherein the inorganic support of the organometallic compound (B) is selected from the group consisting of silica, alumina, mixtures of silica and of alumina, zeolites, natural clays, aluminium silicates, titanium oxide, magnesium oxide, niobium oxide and zirconium oxide.

16. The process of claim 1, wherein the metal of the organometallic compound (B) is bonded to one or more functional groups of the inorganic support.

17. The process of claim 1, wherein the inorganic support is a metal oxide or refractory oxide and the metal of the organometallic compound (B) is bonded to one or more oxygen atoms of the said oxide.

18. The process of claim 1, wherein the organometallic compound (B fixed to the inorganic support corresponds to the formula
in which S is an atom of the inorganic support, M is the metal of the compound (B), R is the at least one hydrocarbon-comprising radical of the compound (B), which if more than one are identical or different from one another, Y is an alkoxy radical or a halogen atom, x is from 1 to 3, y is from 0 to (n−x−1), n is a number representing the oxidation state of the metal M, and z is a number at least equal to 1 and less than or equal to (n−x−y).

19. The process of claim 1, wherein the organometallic compound (B) is fixed to a support comprising a metal oxide or refractory oxide and corresponds to the formula
in which Me is a metal atom of the metal oxide, O an oxygen of said oxide, M is the metal of the compound (B), R is the at least one hydrocarbon-comprising radical of the compound (B), which if more than one are identical or different from one another, Y is an alkoxy radical or a halogen atom, x is from 1 to 3, y is from 0 to (n−x−1), n is a number representing the oxidation state of the metal M, and z is at least equal to 1 and less than or equal to (n−x−y).

20. The process of claim 1, wherein the organometallic compound (B) fixed to the inorganic support is prepared by dispersion over and grafting to the inorganic support of an organometallic precursor (E) having a metal and at least one hydrocarbon-comprising radical bonded to said metal which is identical to said at least one hydrocarbon-comprising radical of the compound (B).

21. The process of claim 20, wherein the organometallic precursor (E) has the general formula

$$MR_{n-y}Y_y$$

in which M is the metal of the compound (B), R is the at least one hydrocarbon-comprising radical of the compound (B), which if more than one are identical or different from one another, Y is an alkoxy radical or a halogen atom, n is a number representing the oxidation state of the metal M and y is from 0 to (n−1), with (n−y) equal to or greater than 1.

22. The process of claim 20 or 21, wherein the grafting is carried out by reacting the organometallic precursor (E) with functional groups of the support.

23. The process of claim 20 or 21, wherein the grafting is carried out by sublimation of the organometallic precursor (E) or by bringing the precursor into contact with the support in a solvent or liquid medium.

24. The process of claim 1, wherein the starting alkane (A) has a number of carbon atoms identical to that of the hydrocarbon-comprising radical of the organometallic compound (B).

25. The process of claim 24, wherein isomeric forms of the starting alkane (A) and of the hydrocarbon-comprising radical of the organometallic compound (B) are different.

26. The process of claim 1, wherein the starting alkane (A) has a number of carbon atoms different from that of the hydrocarbon-comprising radical of the organometallic compound (B).

27. The process of claim 1, wherein the reaction is carried out at a temperature of 20 to 40° C. under an absolute pressure of $10^{-3}$ to 10 MPa.

28. The process of claim 1, including an additional stage carried out before or after the main stage and consisting essentially of a cross-metathesis reaction other than that of the main stage, employing at least one starting alkane (A) other than that used in the main stage, or else an organometallic compound (B) comprising at least one hydrocarbon-comprising radical other than that of the compound (B) used in the main stage, or else, simultaneously, at least one starting alkane (A) and an organometallic compound (B) which are other than those used in the main stage.

29. The process of claim 1, including an additional stage carried out before or after the main stage and consisting essentially of a conventional alkane metathesis reaction employing at least one starting alkane identical to or different from that used in the main stage and brought into contact with a solid catalyst comprising a metal hydride of a metal identical to or different from the metal of the organometallic compound (B) of the main stage.

30. The process of claim 28 or 29, wherein the additional stage is carried out before the main stage, the alkane or alkanes resulting from the additional stage being partially or completely used as starting alkane(s) (A) in the main stage.

31. The process of claim 28 or 29, wherein the additional stage is carried out after the main stage, the flow of the other alkane or alkanes (C) resulting from the main stage being partially or completely used as starting alkane(s) in the additional stage.

* * * * *

UNITED STATES PATENT AND TRADEMARK OFFICE
CERTIFICATE OF CORRECTION

PATENT NO. : 6,469,225 B1  Page 1 of 1
DATED : October 22, 2002
INVENTOR(S) : Basset et al.

It is certified that error appears in the above-identified patent and that said Letters Patent is hereby corrected as shown below:

Column 13,
Line 4, "compound (B" should read -- compound (B) --.
Line 5, after "formula" insert

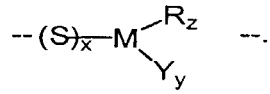

Line 16, after "formula" insert

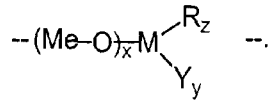

Signed and Sealed this

First Day of July, 2003

JAMES E. ROGAN
*Director of the United States Patent and Trademark Office*